March 11, 1952 C. D. CORLISS Plant Pat. 1,079
EUONYMUS FORTUNEI PLANT
Filed March 15, 1950
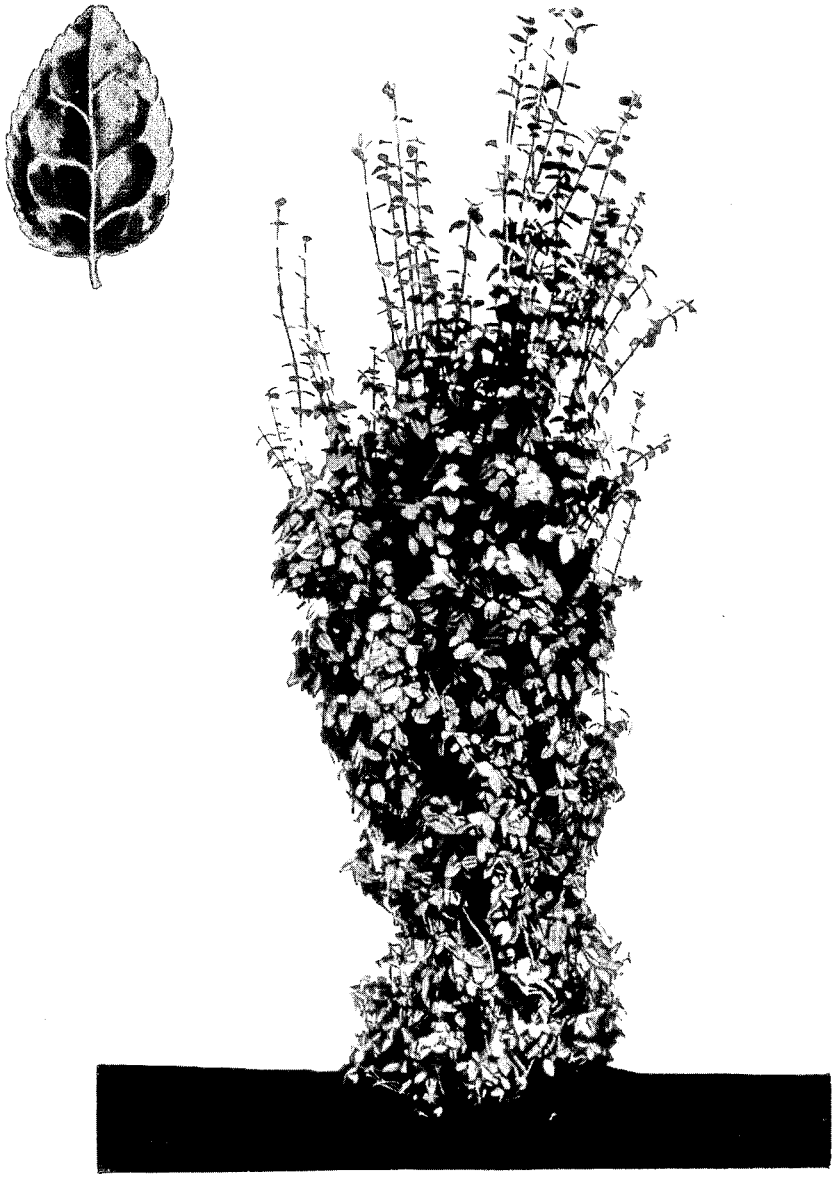
INVENTOR
Clifford D. Corliss
By Orville M. Kile
Plant Pat. Agt.

Patented Mar. 11, 1952

Plant Pat. 1,079

UNITED STATES PATENT OFFICE 1,079

EUONYMUS FORTUNEI PLANT

Clifford D. Corliss, Gloucester, Mass., assignor to Corliss Bros., Inc., Gloucester, Mass., a corporation of Massachusetts Application March 15, 1950, Serial No. 149,865

1 Claim. (Cl. 47—59)

My present invention relates to a new and distinct variety of evergreen Euonymus plant which is one of a series originating from crosses made by me between the varieties *Euonymus fortunei* radicans and *Euonymus fortunei* vegeta.

This new variety is a compact, columnar, broadleaf evergreen as distinguished from its parent varieties which comprise irregular and prostrate plants of open viney growth with spreading horizontal and some nearly procumbent branches and branchlets which grow upright only if supported. The growth habit of my new variety of Euonymus is distinctly fastigiate without support, and the whole plant grows and branches into a perfectly upright columnar form with its lateral branches ascending almost perpendicularly. The form is maintained almost uniformly without shearing, as opposed to the constant training and shearing needed to make a shrub form of its parent varieties.

This new evergreen Euonymus possesses great decorative value in its distinctive bushy columnar habit of growth, in its sturdy character and appearance, and in its natural upright compact columnar growth, forming a uniform shrub with average height of 4 to 5 feet and a spread of approximately 1½ feet. This form makes it very advantageous for use as a hedge plant or as a specimen shrub plant when formal effects are desired.

My new Euonymus plant has an exceptionally strong fibrous root system and the shrub can therefore be easily and successfully transplanted either with bare roots or with a ball of earth surrounding them. The plants grow very successfully in ordinary garden soils and can stand very dry conditions exceedingly well. The variety's scope of usefulness is extended also because of its apparent lack of susceptibility to scale or other diseases since it has never yet been affected by disease, and its hardiness since it has withstood temperatures as low as 20 degrees below zero without even a trace of winter burn.

Asexual reproduction of this variety by cuttings has been accomplished by me at Ipswich, Massachusetts, and the characteristic features have come true and appear to be permanent.

The accompanying illustration depicts a typical plant of my new variety of Euonymus, showing particularly the upright and compact columnar form and the leaves of broad form and lighter veins. In the upper left-hand corner is shown a single older leaf of this variety in approximately true colors.

The known variety most like my new variety is the subject of Plant Patent No. 881, which was also developed by me from the same parent combination. Principal differences are its narrow columnar form and its leaves of lighter green veins.

Following is a more detailed description of this variety, in which color terminology is in accordance with Ridgway's Color Standards and Nomenclature and the usual dictionary meaning.

Growth habit: Variety grows distinctly upright without support. Emanates from a central stem, forming a narrowly columnar shrub which is well bushed at the base. It attains a height of 4 or 5 feet and a spread of approximately 1½ feet. Sturdy in character and appearance.

Branchlets: Dark green; minutely warted. Has tendency to form arial rootlets. Axillary bud short and pointed. Bud-scales imbricated.

Leaves: Opposite; petioled; broad-elliptical to ovate, with obtuse-emarginate apex and acute base. Margins crenate-serrate. 1½ to 3 cm. broad by 2½ to 4½ cm. long. Upper surface of older leaves dark glossy green between Forest and Elm Green (Pl. XVII) with prominent veins considerably lighter green, approximately Biscay Green (Pl. XVII). Under surface dull and lighter green (Biscay Green) than upper surface and with veins less conspicuous than on upper surface. Although the leaf colors are approximately as given, it is to be understood that the claim is merely to glossy, dark green leaves with slightly lighter central vein and under surface. Similar to leaves of the radicans type in its principal color but broader and larger than the leaves of that variety.

Parentage: *Euonymus fortunei* radicans and *Enonymus fortunei* vegeta.

Flowers and berries: None have appeared during the entire fifteen years of the existence of this variety.

Having thus disclosed my invention, I claim:

The new and distinct variety of evergreen *Euonymus fortunei* plant, with combination of features substantially as herein shown and described, characterized particularly by its well-brushed narrowly columnar and fastigiate natural form; its heavy foliage and bushiness and sturdiness of character and appearance; its uniformity of upright columnar form; its extreme hardiness, with absence of any showing of winter burn; its disease resistance, and ability to withstand very dry conditions; and its dark-green glossy leaves with prominent central veins of lighter green.

CLIFFORD D. CORLISS.

REFERENCES CITED

The following references are of record in the file of this patent:

UNITED STATES PATENTS

| Number | Name | Date |
|---|---|---|
| Pl. Pt. 881 | Corliss | Oct. 18, 1949 |

Certificate of Correction

Plant Patent No. 1,079 March 11, 1952

CLIFFORD D. CORLISS

It is hereby certified that error appears in the printed specification of the above numbered patent requiring correction as follows:

Column 2, line 43, for "brushed" read *bushed*;

and that the said Letters Patent should be read as corrected above, so that the same may conform to the record of the case in the Patent Office.

Signed and sealed this 20th day of May, A. D. 1952.

[SEAL]

THOMAS F. MURPHY,
*Assistant Commissioner of Patents.*